United States Patent
LaMoy et al.

(10) Patent No.: US 6,372,184 B1
(45) Date of Patent: Apr. 16, 2002

(54) SHIPBOARD AUTOMATIC LIQUID (CHEMICAL) AGENT DETECTOR

(75) Inventors: Diane M. LaMoy, King George; Michael A. Pompeii; Gregory P. Johnson, both of Fredericksburg; Jonathan A. Byrne, King George; H. Stuart Brooks, Fredericksburg; Marc R. Carlson, Woodbridge; Michael T. Duckett, Fredericksburg, all of VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/613,063

(22) Filed: Jul. 6, 2000

(51) Int. Cl.[7] ................................................ G01N 21/47
(52) U.S. Cl. ..................... 422/82.05; 422/68.1; 356/414
(58) Field of Search ............................... 422/82.05, 58, 422/68.1, 64; 205/775; 356/446, 73, 416, 417, 418, 414

(56) References Cited

U.S. PATENT DOCUMENTS

| | | | |
|---|---|---|---|
| 4,076,420 A | * 2/1978 | De Maeyer et al. ......... 356/73 |
| 4,509,859 A | * 4/1985 | Markart et al. ............. 356/446 |
| 4,516,857 A | 5/1985 | Preston et al. |
| 4,725,733 A | 2/1988 | Horman et al. |
| 4,886,358 A | 12/1989 | Pellenbarg |
| 4,943,929 A | 7/1990 | Simonoff |
| 5,316,727 A | * 5/1994 | Suzuki et al. ............... 422/68.1 |
| 5,336,467 A | * 8/1994 | Heidt et al. .................... 422/64 |
| 5,350,922 A | 9/1994 | Bartz |
| 5,493,730 A | 2/1996 | Vo-Dinh |
| 5,597,532 A | * 1/1997 | Connolly ...................... 422/58 |
| 6,217,744 B1 | * 4/2001 | Crosby ........................ 205/775 |
| 6,261,522 B1 | * 7/2001 | Hough et al. ............ 422/82.05 |

* cited by examiner

Primary Examiner—Jill Warden
Assistant Examiner—Brian J. Sines
(74) Attorney, Agent, or Firm—James B. Bechtel, Esq.; John P. McMahon, Esq.

(57) ABSTRACT

A system for detecting chemical warfare agents is disclosed. The system uses a detector paper that stains upon contact with liquid chemical agent droplets and spectrophotometry technology, in cooperation with a spectral filter wheel, and a processor, to analyze the stain and determine if the stain is created by a chemical warfare agent.

5 Claims, 3 Drawing Sheets

US 6,372,184 B1

SHIPBOARD AUTOMATIC LIQUID (CHEMICAL) AGENT DETECTOR

STATEMENT OF GOVERNMENT INTEREST

The invention described herein may be manufactured and used by or for the Government of the United States of America for governmental purposes without the payment of any royalties thereon or therefor.

BACKGROUND OF INVENTION

1. Field of Invention

The present invention relates to a system used to analyze compositions to determine what chemical elements are present therein and, more particularly, to a system that analyzes liquid droplets present in the air and, if undesired liquid chemical agents are present therein, provides signals to activate alarms.

2. Description of the Prior Art

The ambient by which one is surrounded is of utmost importance. However, the ambient may suffer from pollution that allows the surrounding atmosphere to be contaminated, especially by man-made waste and vapor pollutants. The environment by which one is surrounded may also be invaded by more serious pollutants, especially during terrorist situations or during warfare, in particular, biological warfare. Biological warfare involves the use of liquid chemical agents comprising living organisms (as disease germs) or their toxic products, such as blister and nerve chemical agents, that attack humans, animals or plants, with the human suffering severe bodily pain.

Various systems that monitor for the presence of nerve gases are known in the prior art. These systems serve well their intended purpose and measure vapor samples, but it is further desired to provide a system that measures liquid chemical agents such as in the form of droplets to detect for the presence of warfare agents therein. Systems that measure concentration of samples, such as chemical warfare nerve agents are disclosed in U.S. Pat. Nos. 4,516,857 ('857); 4,725,733 ('733); 4,886,358 ('358); and 4,943,929 ('929) all of which are herein incorporated by reference. These systems also serve well their intended purpose, especially those of the '857 and '358 patents that employ spectrometers. It is further desired to use spectrophotometry technology, in operative cooperation with light filtering techniques, to analyze chemical agent droplets for the presence of chemical warfare agents therein, such as nerve or blister warfare agents.

OBJECTS OF THE INVENTION

It is a primary object of the present invention to provide a system utilizing spectrophotometry technology that accurately detects and monitors for the presence of undesired chemical agent liquids in an environment.

It is another object of the present invention to provide a system employing spectrophotometry technology that quickly, yet accurately, detects and monitors for the presence of undesired chemical liquids in an environment and, upon detection thereof, provides an alarm indication.

Another object of the present invention is to provide a system that uses spectrophotometry technology, in particular, first and second optical scanners that operatively cooperate with a processor and a paper sensitive to chemical agent liquid droplets that detect for the presence of chemical warfare agents.

Further, it is an object of the present invention to provide a system utilizing spectrophotometry technology in operative cooperation with light filtering techniques to detect for the presence of dangerous chemical warfare agents.

Furthermore, it is an object of the present invention to provide for an optical scanner that generates an electrical signal which is routed to means for comparing the electrical signal against predetermined signals indicative of unwanted and/or dangerous compositions, and if a match exists therebetween, an alarm is generated.

SUMMARY OF THE INVENTION

This invention is directed to a system for sampling the ambient of a selected environment for the presence of unwanted, predetermined chemical liquid agents therein. The system comprises paper, spectrophotometry means, and means for comparing. The paper stains upon contact with liquid chemical agent droplets. The spectrophotometry means generates a first digital signal serving as a first digital signature representative of the stain. The means for comparing compares the first digital signal against predetermined digital signals, each representative of a particular liquid chemical agent, and generates an alarm if there is a match between the first digital signature and the predetermined digital signals.

BRIEF DESCRIPTION OF THE DRAWINGS

A better understanding of the present invention may be realized when considered in view of the following detailed description, taken in conjunction with the accompanying drawings wherein.

DETAILED DESCRIPTION OF PREFERRED EMBODIMENTS

Figure 1:
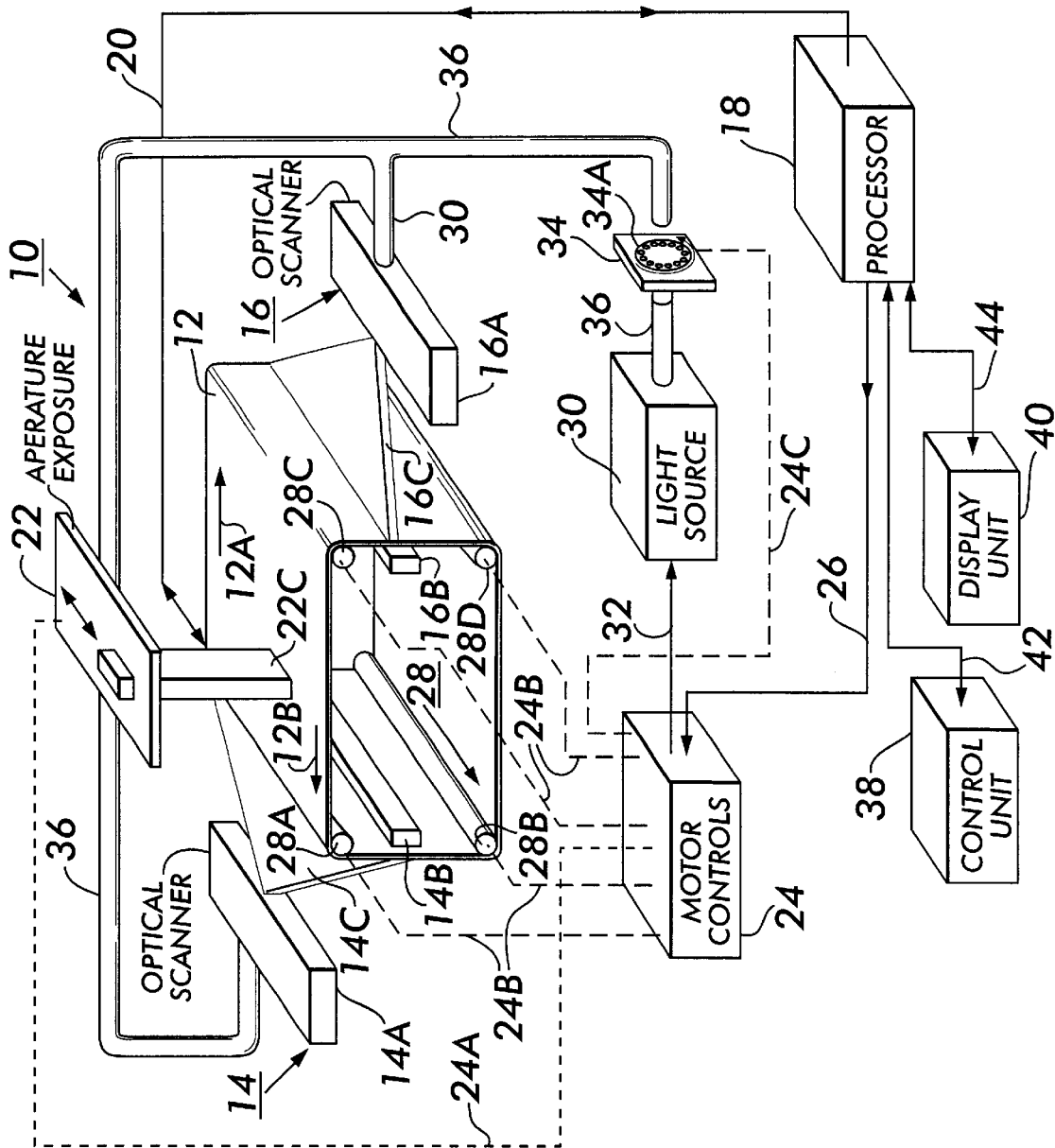
FIG. 1 is a block diagram of the system of the present invention.

Referring to the drawings, wherein the same reference number is used to indicate the same element throughout, there is shown in FIG. 1 a block diagram of a system 10 herein termed "shipboard automatic liquid (Chemical) agent detector (SALAD)" which is a fixed point detection system designed for the continuous operation to detect chemical warfare agents. Chemical agents considered to pose the greatest threat are the nerve and blister agents.

The system 10 comprises detector paper 12 that is moveable in first and second directions 12A and 12B, and spectrophotometry equipment including an optical scanner 14 comprising elements 14A and 14B and generating an optical beam 14C, and an optical scanner 16 comprising elements 16A and 16B and generating an optical beam 16C. The optical scanners 14 and 16 are each serviced by a processor 18 by way of digital path 20. The system 10 further comprises an aperture exposure 22, motor controls 24 that are serviced by the processor 18 via control path 26, and a cassette driver 28 that holds and moves the paper 12 by means of drive rollers 28A, 28B, 28C and 28D. The motor controls 24 provide light source 30 with excitation by way of signal path 32.

The system 10 further comprises a spectral filter wheel 34 that is interposed between the light source 30 and the optical scanners 14 and 16. The spectral filter wheel 34 has a plurality of selectable light filters, one of which is generally indicated as 34A. The light source 30, the spectral filter wheel 34 and the optical scanners 14 and 16 are interconnected by an optical light path comprised of optical fiber cable 36. The system 10 further comprises a control unit 38 and a display unit 40 that are serviced by the processor 18 via control paths 42 and 44 respectively.

The detector paper 12 is typically a 200 foot replaceable roll of M8detectable paper. The M8paper is known in the prior art and was supplied by Anachemia Chemical, 255 Norman, Ville St. Pierre, Qc. H&R 1A3, Canada. The paper is specified by MIL-P-51409. The dyes used in the paper are specified in MIL-D-1410 (green dye). MIL-D-41411 (yellow dye) and, MIL-D-41412 (red dye). To extend paper life, the roll is double spooled so that the paper can be moved bi-directionally, that is, in both directions 12A and 12B. The M8detectable paper roll 12 is specially treated so as to detect nerve and blister chemical warfare agents.

The optical scanners 14 and 16 provide an optical beam 14C or 16C, respectively, that intercepts a stain present on the paper 12 as it is being moved in its first or second direction 12A and 12B respectively. More particularly, the optical scanner 16 detects the stain when the paper is moved in direction 12A and, conversely, the optical scanner 14 detects the stain when the paper is moved in direction 12B. Each of the optical scanners 14 and 16 has means for receiving the optical beam after is has passed through the paper 12 and providing an electromagnetic spectrum representative of the chemical composition of the stain. Each of the optical scanners have means, such as a detector comprised of charge coupled devices (CCDs), for converting the electromagnetic spectrum into a first digital signal serving as a first digital signature of the stain. Each of the optical scanners 14 and 16 comprises a CCD camera for imaging the optical beams 14C and 16C respectively. Each of the optical scanners 14 and 16 also have video frame grabbers that convert the optical images in their analog form into corresponding digital signals.

Aperture exposure 22 has means for being opened and closed and is interposed between the paper 12 and the air being sampled. When the aperture 22 is in its opened position, it allows the air, and any moisture or droplets therein, to fall onto a zone 22C generally illustrated in FIG. 1. The aperture exposure 22 is provided with drive means, included as part of motor controls 24, which is responsive to the presence and absence of a first control signal on signal path 26 for respectively opening and closing the aperture exposure 22. The motor controls 24 may have high voltage electronics to move the aperture exposure 22 and also may have a linear power supply that supplies power to the light source 30 on signal path 32.

The motor controls 24 also includes applying signals on control line 24B that control the driver rollers 28A, 28B, 28C and 28D of the cassette drive 28 so that the paper 12 may be guided passed the aperture exposure 22 and into the line of sight of optical scanners 14 and 16, in particular, into the respective viewing apertures of the CCD cameras of the optical scanners 14 and 16. The cassette drive 28 is preferably designed so that the detector paper 12 or cassette comprising the paper 12 can be removed and replaced. The motor controls 24 also provides a control signal to the spectra filter wheel 34 by way of control line 24C. The spectra filter wheel 34 may be rotated to a desired position preferably in response to a stepping motor within the motor controls 24.

The light source 30 is preferably a halogen lamp that provides illumination to both the optical scanners 14 and 16 concurrently by way of fiber optic cable 36. More particularly, the halogen lamp 30 provides illumination by way of the fiber optic cable 36, through the spectral filter wheel 34, and then onto the optical scanners 14 and 16.

The spectral filter wheel 34 is known in the art and one such spectral filter wheel is described in the previously incorporated by reference U.S. Pat. No. 4,725,733. The spectral filter wheel 34 is preferably provided with thirteen (13) different narrow-band and band pass filters 34A. Each filter 34A is singly positioned in front of the light source 30 and permits specific wavelengths of light to pass therethrough, each occupying a specific portion of the electromagnetic spectrum. For each filter 34A, the beam 14C or 16C is specially conditioned for that specific wavelength of that particular filter 34A. Each of the thirteen (13) filters is selectable by the stepping motor of the motor controls 24 stepping the spectra filter wheel 34 into a position corresponding to the particular filter 34A that is desired. The operation of the system 10 may be further described with reference to FIG. 2.

In general, the system 10 has two separate modes of operation with the first being the set-up or calibration mode, wherein each of the thirteen (13) filters 34A of the spectral filter wheel 34 is selected and camera video data is digitized for an unstained detector paper 12 and then stored in a reference or library table in the processor 18. The unstained detector paper 12 is moved, by way of control from motor controls 24, in direction 12A into the field of view of optical scanner 16 and then moved, again by control from the motor controls 24, in direction 12B into the field of view of optical scanner 14.

When a stain is introduced, that is, when detector paper 12 comes into contact with liquid droplets, the digital video data, generated by the appropriate optical scanner 14 or 16, is compared to the unstained reference data for each of the thirteen (13) filters. The result is a reflectance ratio for each of the filter positions.

Each agent stain has a unique pattern of reflectant ratios, also called its signature, which permits the detection/differentiation of the liquids of the nerve and blister chemical agents. In addition, stains from unknown substances can be disregarded if their signatures do not match those of the agent library table. In operation, the system continuously advances the detector paper 12, by means of cassette drive 26 past the aperture exposure 22 exposing the paper 12 to liquid chemical agent droplets in the atmosphere. If the droplets land on the paper 12 they chemically react with dyes embedded in the paper to create a colored stain that occupies a region 22C on the paper 12. The detector paper 12 advances into the field of view while the optical scanners 12 or 16 each have a CCD camera where it is imaged thereon using up to thirteen (13) separate colors of illumination provided by the spectral filter wheel 34.

Figure 2:
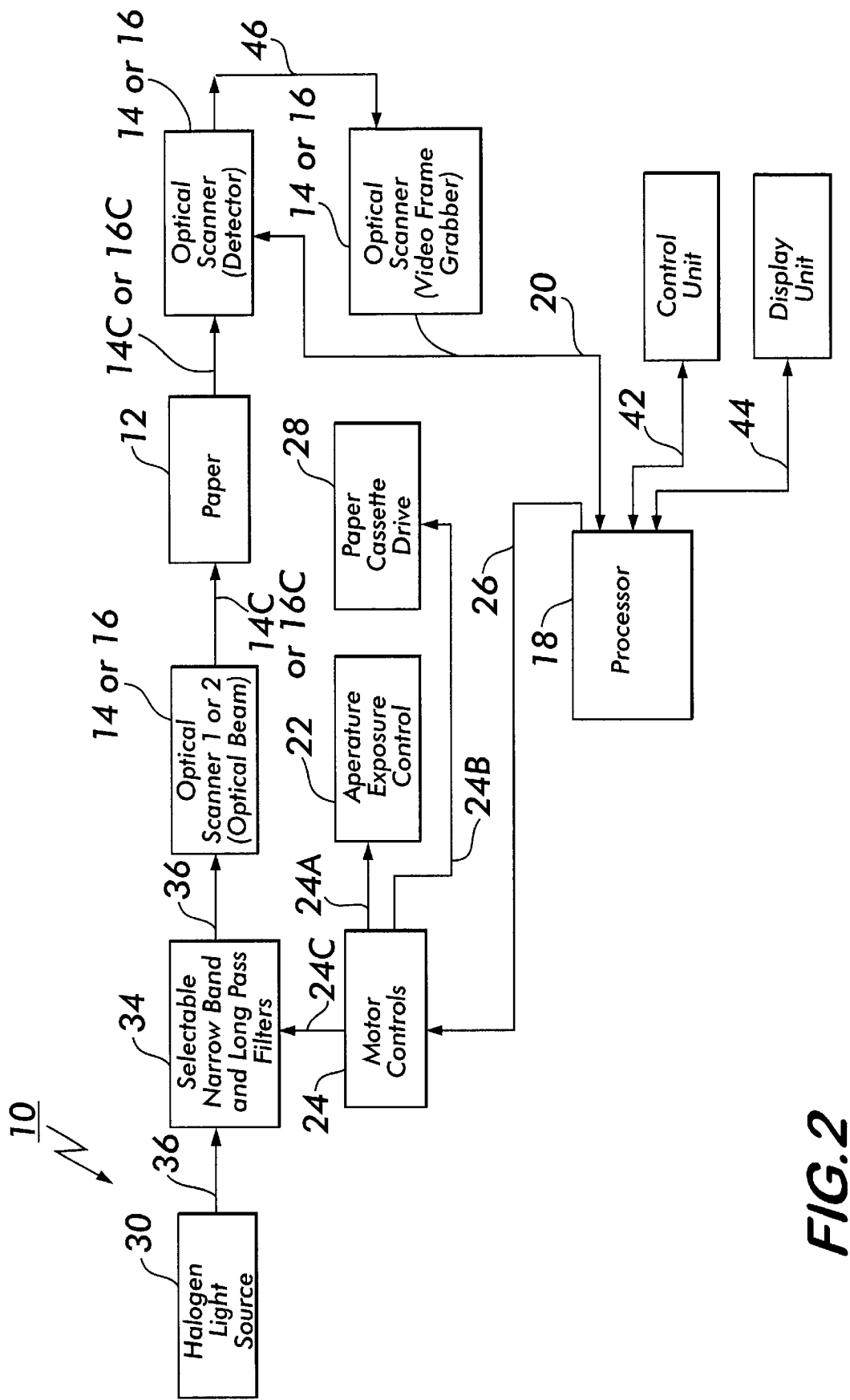
FIG. 2 is a schematic illustrating further details of the system of FIG. 1.

With reference to FIG. 2, the processor 18 provides a control signal on path 26 which causes the motor control 24 to cause the rotation of the spectral filter wheel 34 to its first position. The output of the halogen light source 30 now passes through and is customized by the selected filter 34A so as to provide selected light excitation to the optical scanner 14 or 16. The optical scanner 14 or 16 provides an optical beam 14C or 16C of the first color associated with the first of filters 34A that is selected which, in turn, intercepts the stain passing through its field of vision. The optical beam 14C or 16C, after it passes through the paper, is captured by a CCD array of the camera of the appropriate scanner 14 or 16 which stores, in a sequential manner, the pattern of charges indicative of the optical beam 14C or 16C which, in turn, is indicative of the chemical composition of the stain. These sequential patterns are read out via signal path 46 to the optical scanner 14 or 16, in particular, to the video frame grabbers thereof. The video frame grabbers provide a digital signal representative of the electromagnetic spectrum contained in the optical beam 14C or 16C after it had passed through the detector paper 12, in particular, the stain occupied by region 22C. The digital signal from either optical scanner 14 or 16 is directed onto signal path 20 that is applied to the processor 18.

The processor 18 then initiates the proper control signal on control line 26 which causes the motor control 24 to move the spectral filter wheel 34 to its second filter so as to provide a second color to energize the same stain occupying the same region 22C that is still within the field of view of the appropriate optical scanner 14 or 16. The optical scanner then processes the second colored illumination, in the same manner as the first colored illumination, and directs this information back to the processor 18 via signal path 20. The processor 18 repeats the same process until all thirteen (13) colors that are made available by the operation of the spectral filter wheel 34 have been exercised to impinge onto the stain occupying region 22C. The processor 18 then compares each of the corresponding thirteen (13) digital signals against a stored agent library to determine if any of the thirteen (13) digital signals corresponding to a digital signal matching a nerve and blister agent. The overall operation 48 of the present invention may be further described with reference to FIG. 3.

Figure 3:
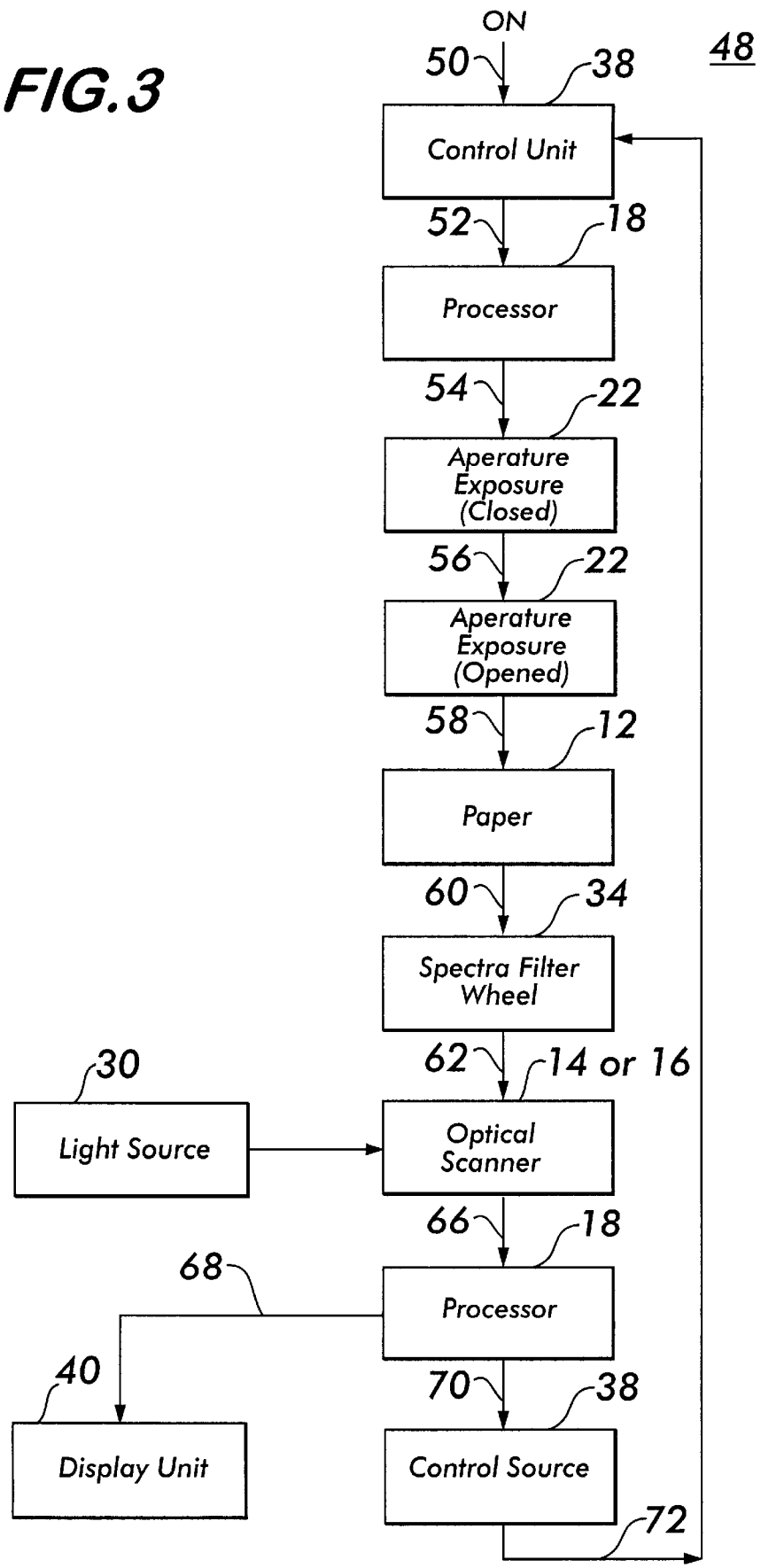
FIG. 3 is a flow diagram of the overall operation of the system of FIG. 1.

As seen in FIG. 3, the overall operation 48 is initiated by the operator generating the command ON on signal path 50 from the control unit 38 which, in turn, provides a control signal on signal path 52 to the processor 18. The processor 18 initiates, on signal path 54, the automatic exposure door opening causing the closed aperture 22 to be requested to be opened as indicated on signal path 56 which is recognized by the aperture exposure control 22 so that the aperture is opened as indicated on signal path 58 and the detector paper 12 is exposed to the atmosphere. The detector paper 12 collects the droplets in the air and advances the stain occupying region 22C, into the CCD camera's view of the appropriate scanner 14 or 16. The optical scanner 14 or 16 is energized by a light source 30 providing the filtered light onto the paper 12 as indicated by signal path 60. The CCD camera of the appropriate scanner 16 or 18 outputs video data for the thirteen (13) different filter colors which are provided for by the processor 18 causing the spectral filter wheel 34 to move through its thirteen (13) different positions, as indicated by signal path 62, in a manner as previously described. The optical scanner 14 or 16 then digitizes the video data and causes the processor 18 to initiate its detection routine as indicated by signal path 66. If an agent stain is detected, the information is sent to the display unit 40 as indicated by signal path 68, and to the control unit 38 as indicated by signal path 70. The control unit 38 then sequences back, as indicated by signal path 72, to its initial condition waiting for another "ON" command.

It should be appreciated that the practice of the present invention provides for a system that detects for the presence of chemical agent droplets in the environment and upon such detection provides an alarm signal. It should be further appreciated that the practice of the present invention provides for a system that utilizes thirteen (13) different colors to accurately differentiate between chemical agent droplets so as to detect for the unwanted and dangerous chemical agent droplets comprising nerve or blister agents.

It should be also understood that the practice of the present invention provides for spectrometry technology that quickly yet accurately detects and monitors for the presence of undesired chemical liquids in an environment and upon detection thereof provides an alarm indication thereof.

Although the invention has been described relative to specific embodiments thereof, there are, however, numerous variations and modifications that become readily apparent to those skilled in the art in light of the above disclosure. It is, therefore, to be understood that within scope of the claims the invention may be practices other than that specifically disclosed herein.

The invention claimed:

1. A system for detecting the presence of liquid chemical agent droplets in air comprising:

(a) paper that stains upon contact with said liquid chemical agent droplets;

(b) an aperture exposure located above said paper and having means for being opened and closed and interposed between said paper and said air;

(c) aperture exposure drive means operatively connected to said aperture exposure and serving as said means for being opened and closed and responsive to the presence and absence of a first control signal generated by an external control circuit for respectively opening and closing said aperture exposure;

(d) a cassette for holding said paper;

(e) cassette drive means responsive to the presence of second and third controls signals generated by said external control circuit for respectively moving said paper in first and second directions that are opposite from each other;

(f) at least a first optical scanner providing a first optical beam and arranged so that said first optical beam intercepts said stain as said paper is being moved in said first direction in response to said second control signal, said first optical scanner having means for receiving said optical beam after it has passed through said paper and providing an electromagnetic spectrum representative of the chemical composition of said stain, said first optical scanner having means for converting said electromagnetic spectrum into a first digital signal serving as a first digital signature of a stain;

(g) a light source applied to said first optical scanner serving as the excitation for said first optical beam;

(h) a spectral filter wheel with rotatable means and having a predetermined number of selectable filters, said spectral filter wheel being interposed between said light source and said first optical scanners;

(i) spectral filter wheel drive means connected to said rotatable means and responsive to a fourth control signal generated by said external control circuit so that said filters are selectively interposed between said light source and said first optical scanner; and (j) means for receiving and comparing said first digital signal against predetermined digital signals each representative of a particular liquid chemical agent and generating an alarm if there is a match between said first digital signal and any of said predetermined digital signals.

2. The system of claim 1 further comprising:

a second optical scanner receiving said excitation from said light source and providing a second optical beam and arranged so that said optical beam intercepts said stain as said paper is being moved in said second direction in response to said third control signal, said second optical scanner having means for receiving said second optical beam after it has passed through said paper and providing an electromagnetic spectrum representative of the chemical composition of said stain, said second optical scanner having means for converting said electromagnetic spectrum into said first digital signal serving as said first digital signature of said stain.

3. The system of claim 2, wherein said light source, said spectral filter wheel, and said first and second optical scanners are interconnected by an optical cable.

4. The system of claim 2, wherein each of said first and second optical scanner comprises a CCD camera for imaging said optical beam after it passes through said stain and a video frame grabber for providing said first digital signal.

5. The system according to claim 2, wherein said predetermined number of said selectable filters is thirteen (13) and each of which selectable filters provides a separate color for said first and second optical beams intercepting stain on said paper and corresponding providing said first digital signal so that a total of thirteen (13) first digital signals serves as said first digital signature of said stain.

\* \* \* \* \*